United States Patent
Thompson

(12) United States Patent (10) Patent No.: US 7,084,402 B2
Thompson (45) Date of Patent: Aug. 1, 2006

(54) LIQUID COUPLED DEFECT DETECTION SYSTEMS AND METHODS

(75) Inventor: Jeffrey G. Thompson, Kent, WA (US)

(73) Assignee: The Boeing Company, Chicago, IL (US)

( * ) Notice: Subject to any disclaimer, the term of this patent is extended or adjusted under 35 U.S.C. 154(b) by 295 days.

(21) Appl. No.: 10/721,707

(22) Filed: Nov. 25, 2003

(65) Prior Publication Data

US 2005/0109941 A1 May 26, 2005

(51) Int. Cl.
*G01N 21/88* (2006.01)
(52) U.S. Cl. .................... 250/341.6; 250/341.1
(58) Field of Classification Search ............ 250/341.6, 250/341.1; 702/84
See application file for complete search history.

(56) References Cited

U.S. PATENT DOCUMENTS

| | | | |
|---|---|---|---|
| 4,391,281 A * | 7/1983 | Green | 600/446 |
| 5,101,382 A * | 3/1992 | Yamanaka | 367/7 |
| 5,476,010 A | 12/1995 | Fleming et al. | |
| 6,040,900 A | 3/2000 | Chen | |
| 6,041,020 A | 3/2000 | Caron et al. | |
| 6,236,049 B1 | 5/2001 | Thomas et al. | |
| 6,399,948 B1 | 6/2002 | Thomas et al. | |
| 6,437,334 B1 | 8/2002 | Thomas et al. | |
| 6,847,907 B1 * | 1/2005 | Novotny | 702/84 |
| 2002/0018510 A1 | 2/2002 | Murphy et al. | |
| 2002/0172410 A1 | 11/2002 | Shepard | |

FOREIGN PATENT DOCUMENTS

| | | |
|---|---|---|
| DE | 101 47 102 A | 4/2003 |
| EP | 0 492 559 | 7/1992 |
| JP | 63 025039 | 2/1988 |
| JP | 01 078125 | 3/1989 |
| WO | WO 94/01766 | 1/1994 |
| WO | WO 00/66004 | 11/2000 |
| WO | WO 01/20319 | 3/2001 |
| WO | WO 02/089042 | 11/2002 |
| WO | WO 03/019175 | 3/2003 |

OTHER PUBLICATIONS

U.S. Appl. No. 10/324,014, filed Dec. 20, 2002, Thompson et al.
Article entitled Non-destructive Testing Applications in Commercial Aircraft Maintenance, 10 pages, www.ndt.net/article/ecndt98/aero/031/031.htm.
Aricle entitled Emerging NDE Technologies and Challenges at the Beginning of the 3$^{rd}$ Millennium—Part I, Part II, 18 pages, www.ndt.net/article/v05n01/barcohen/barcohen.htm.

(Continued)

*Primary Examiner*—Otilia Gabor
(74) *Attorney, Agent, or Firm*—Harness Dickey & Pierce P.L.C.

(57) ABSTRACT

Systems and methods for detecting defects in a test specimen. The method generally includes applying a liquid detection medium to the test specimen and exciting the test specimen to cause the liquid detection medium to produce a defect signature for a defect in the test specimen. The liquid detection medium is monitored for defect signatures produced by the liquid detection medium.

29 Claims, 3 Drawing Sheets

OTHER PUBLICATIONS

Article entitled Thermographic Quality Assurance of Turine Engine Components, 3 pages, www.reliabilityweb.com./excerpts/excerpts/infrared_turbine.pdf.

Patent Abstracts of Japan, vol. 012, No. 227, (M-713), Jun. 28, 1988 & JP 63 025039 A, (Mitsubishi Heavy Ind. Ltd), Feb. 2, 1988, (Feb. 2, 1988) abstract, Japan.

Patent Abstracts of Japan, vol. 013, No. 303 (P-896), Jul. 12, 1989 & JP 01 078125 A (NKK Corp.), Mar. 23, 1989, abstract, Japan.

"NDT of polymer materials using lock-in thermography with water-coupled ultrasonic excitation," Rantala, J., et al, NDT & E International, Butterworth-Heinemann, Oxford, GB, vol. 31, No. 1, Feb. 1998, pp. 43-49, XP004292560, ISSN: 0963-8695.

"Installation and application of ultrasonic infrared thermography", Yi Hong et al, Acoustical Science and Technology Acoust., Soc. Japan, vol. 25, No. 1., Nov. 14, 2002, pp. 77-80, XP002313448, Nanjing, China, China-Japan Joint Conference on Acoustics 2002 (JCA2002).

PCT International Search Report, PCT/US2004/036293, Jan. 27, 2005, 5 pages.

Written Opinion of the International Searching Authority, PCT/US2004/036293, Jan. 27, 2005, 11 pages.

* cited by examiner

LIQUID COUPLED DEFECT DETECTION SYSTEMS AND METHODS

FIELD OF THE INVENTION

The present invention relates to nondestructive inspection (NDI) techniques, and more particularly to liquid coupled defect detection systems and methods.

BACKGROUND OF THE INVENTION

Nondestructive inspection (NDI) techniques are used to examine in-service and production aircraft parts for defects such as delaminations, disbonds, cracks, and corrosion. Indeed, as the existing aircraft fleet ages requiring more frequent inspections and new materials and structures are introduced on new aircrafts, the use of NDI techniques will likely remain prevalent in the aerospace industry as well as other industries.

SUMMARY OF THE INVENTION

The present invention relates to liquid coupled defect detection systems and methods. In a preferred implementation, a method of detecting defects in a test specimen generally includes applying a liquid detection medium to the test specimen; exciting the test specimen to cause the liquid detection medium to produce a defect signature for a defect in the test specimen; and monitoring the liquid detection medium for defect signatures produced by the liquid detection medium.

In another preferred implementation, a method of detecting defects in a test specimen generally includes applying a liquid couplant to at least a first surface portion of the test specimen; acoustically exciting the test specimen; and monitoring the liquid couplant to detect vibration effects on the liquid couplant which indicate defects in the test specimen. The vibration effects can include at least one of a standing wave of liquid couplant on the first surface portion and an ejection of liquid couplant from the first surface portion.

In another preferred implementation, a system for detecting defects in a test specimen generally includes a liquid couplant applied to the test specimen. The system also includes an exciter coupled to the test specimen to excite the test specimen and cause the liquid couplant to produce a defect signature for a defect in the test specimen. The system further includes a device for detecting defect signatures produced by the liquid couplant in response to the excitation.

The features, functions, and advantages can be achieved independently in various embodiments of the present inventions or may be combined in yet other embodiments.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiment(s) is merely exemplary in nature and is in no way intended to limit the invention, its application, or uses.

According to one aspect, the invention provides methods for detecting defects (e.g., disbonds, delaminations, etc.) in a test specimen. In one embodiment, a method generally includes applying a liquid detection medium or couplant to the test specimen; exciting the test specimen to cause the liquid detection medium to produce a defect signature for a defect in the test specimen; and monitoring the liquid detection medium for defect signatures produced by the liquid detection medium.

Figure 1:
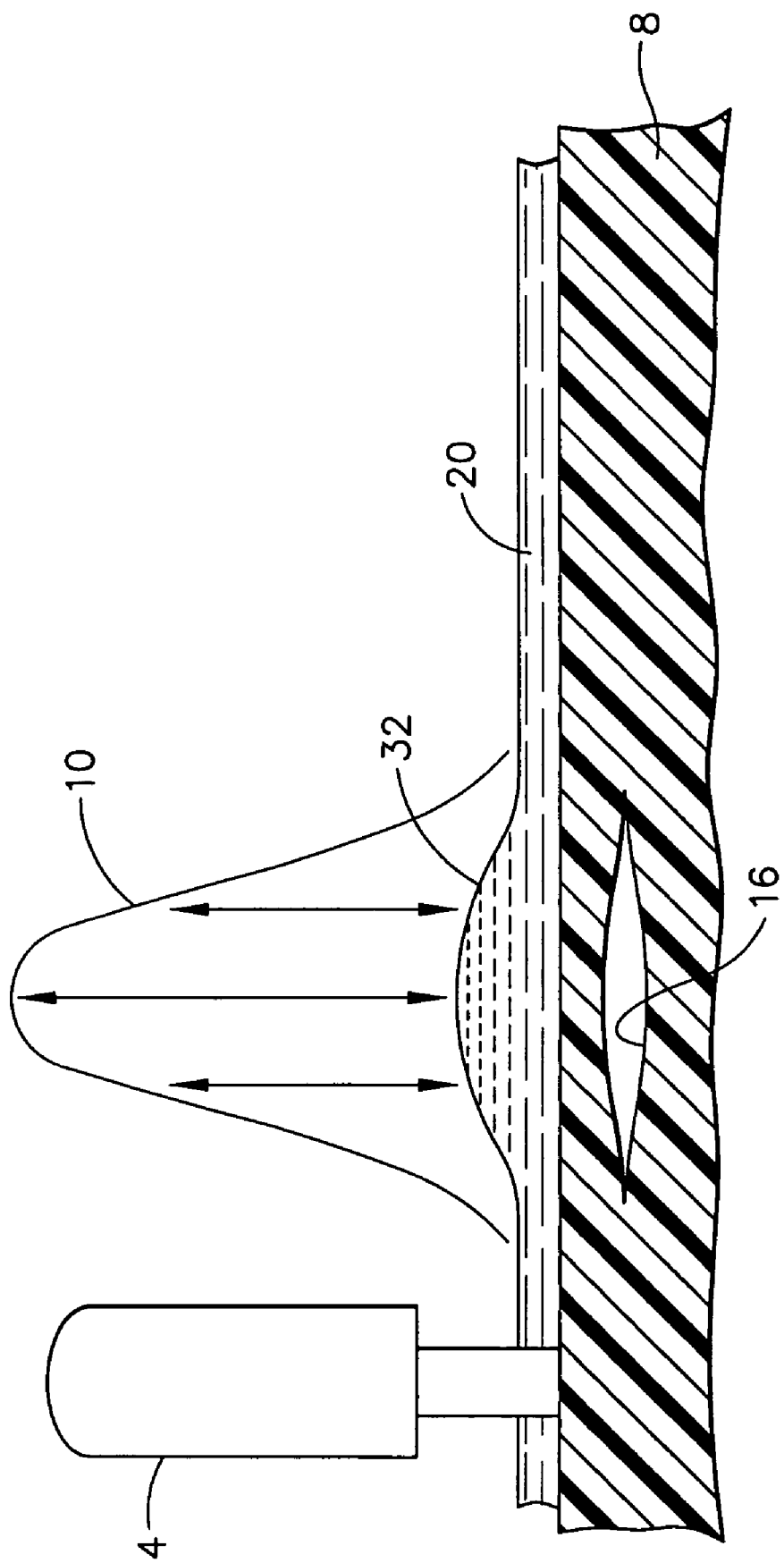
FIG. 1 is a schematic illustrating a test specimen being excited with an excitation source according to one embodiment of the invention.
Figure 2:
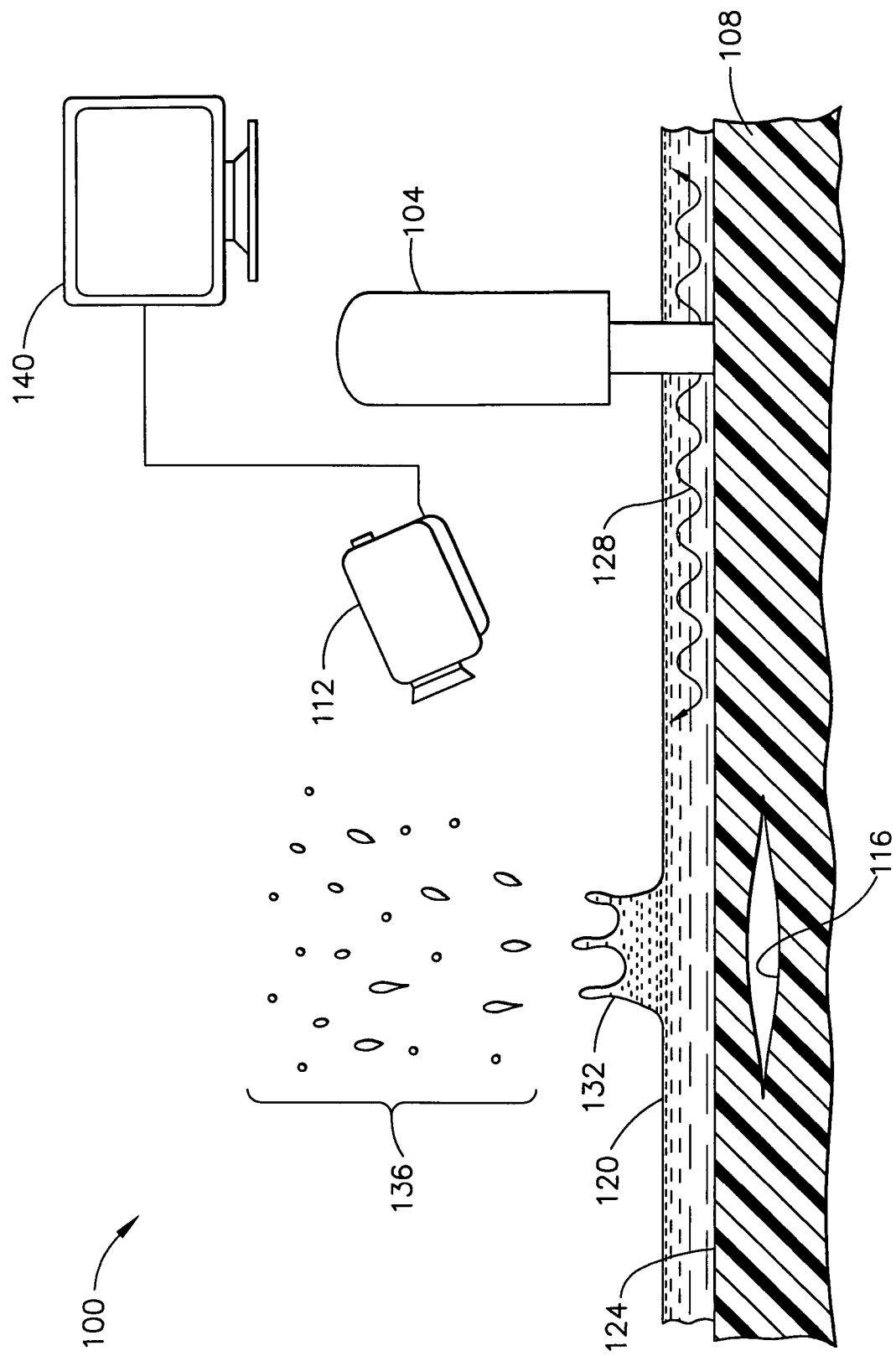
FIG. 2 is a schematic of a liquid coupled defect detection system according to one embodiment of the invention.
Figure 3:
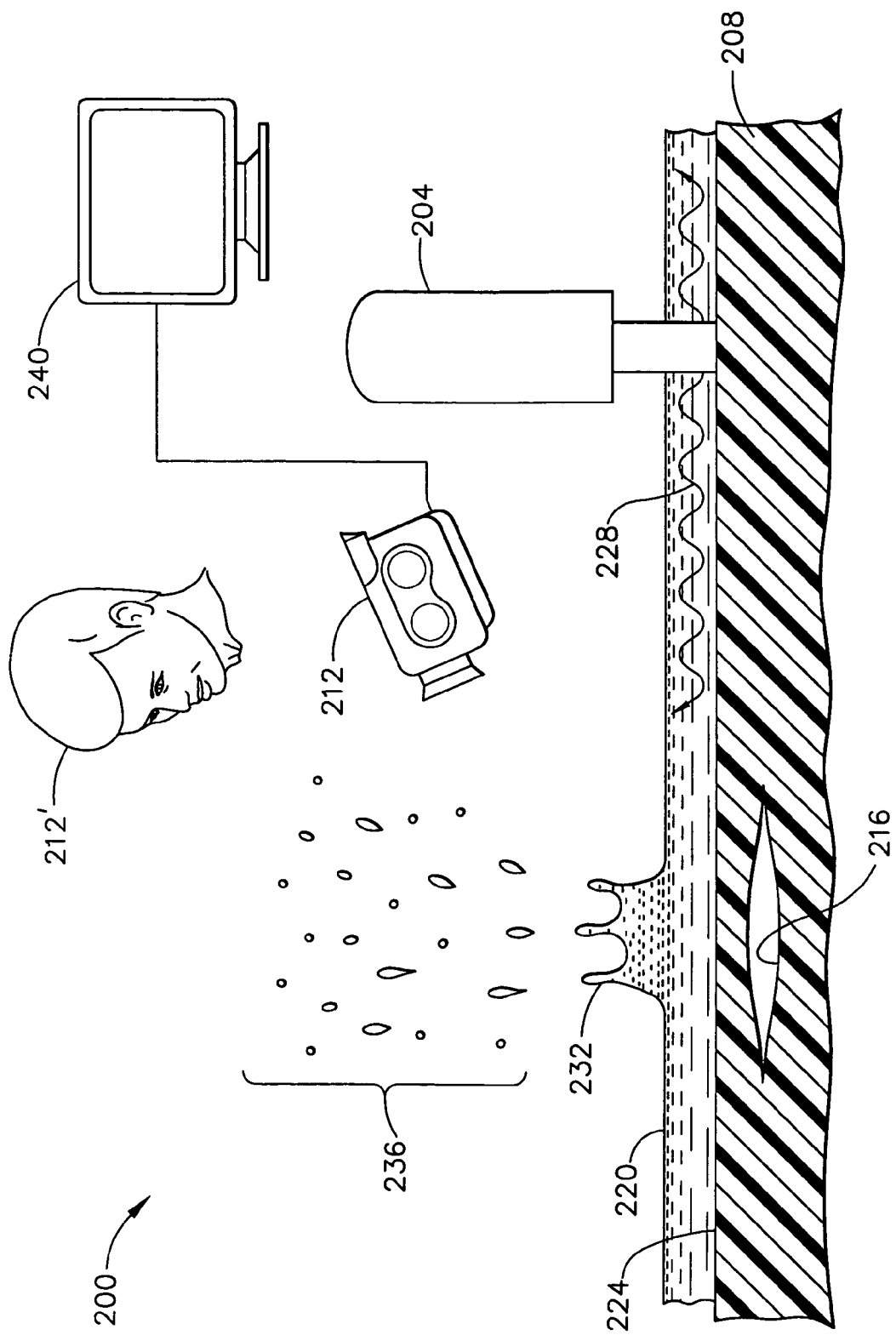
FIG. 3 is a schematic of a liquid coupled defect detection system according to another embodiment of the invention.

In response to the excitation, the liquid couplant can produce various defect signatures which indicate the presence of defects in the test specimen. For example, FIG. 1 illustrates a test specimen 8 being excited with an excitation source 4. A preferential high amplitude vibration 10 is disposed generally above a defect 16 in the test specimen 8 due to the decreased stiffness at the defect 16 and greater localized bending generally above the defect 16. As shown in FIG. 1, the vibration 10 couples with the liquid couplant 20 to form a standing wave 32 of couplant 20 generally above the defect 16. The preferential high amplitude vibration can also cause couplant to be ejected or atomized (a "geyser" effect) from the test specimen, as shown in FIGS. 2 and 3. Accordingly, standing waves and "geysers" are two types of defect signatures the detection of which indicates existence of one or more defects in the test specimen.

Another example of a defect signature is a cold signature produced by a cooling effect of the agitated couplant and/or by a cooling effect of ejected couplant as it evaporates. Detection of such a cold signature, for example with an infrared camera, indicates existence of a defect in the test specimen.

An exemplary system 100 embodying at least one aspect of the invention is illustrated in FIG. 2. As shown in FIG. 2, the system 100 includes an excitation source 104 for exciting the test specimen 108. Preferably, the excitation source 104 is an ultrasonic energy source, such as an ultrasonic welder. Alternatively, other excitation sources can be employed such as mechanical shakers and acoustic horns.

The system 100 also includes an infrared camera 112 for detecting cold signatures produced by a cooling effect of the agitated couplant and/or by a cooling effect of ejected couplant as it evaporates. Alternatively, a wide range of other devices and techniques can be used for detecting the defect signatures or vibration effects of the liquid couplant in response to the excitation including high speed photography, videography for motion analysis, specialized lenses, high speed analysis lighting, video imaging technologies, and specialized techniques such as Schlieren, streak, and pulsed laser illumination.

In an exemplary embodiment, the liquid couplant 120 applied to the test specimen 108 is water. In other embodiments, a wide range of other liquid couplants, preferably liquids non-reactive and non-contaminating to the test specimen, can be used including oils, glycerins, high purity alcohols, non-contaminating liquid chemicals, etc.

In some embodiments, insoluble particles (e.g., relatively heavy magnetic material) can be entrained in the liquid couplant. The insoluble particles can form tiger-striped patterns or other patterns on the test specimen which are visible even after the excitation of the test specimen has stopped. Accordingly, the patterns produced by the insoluble material can thus provide an indication of a location of a defect even after excitation has stopped.

The selection of a particular liquid couplant can be based on one or more various factors. For example, a particular liquid couplant may be selected to encourage evaporation of the liquid couplant after its ejection from the test specimen. Or for example, a particular liquid couplant may be selected to minimize (or at least reduce) absorption of the couplant into the test specimen, to minimize (or at least reduce) entrapment of the couplant into the test specimen, and/or to minimize (or at least reduce) contamination of the test specimen by the couplant.

In operation, the system 100 can be used as follows to detect defects in the test specimen 108. A liquid couplant 120 is applied to at least a first surface portion 124 of the test specimen 108. In an exemplary embodiment, the liquid couplant is water misted onto the surface portion 124 with a spray bottle.

The test specimen 108 is excited with the excitation source 104. In the illustrated embodiment, the test specimen 108 is acoustically excited with a preferably high energy ultrasonic source in contact with the test specimen 108. The source 104 preferably applies ultrasonic energy 128 to the test specimen 108 which propagates through the test specimen 108. The propagating energy 128 causes preferential, large amplitude vibrations generally above a defect 116 in the test specimen 108. The increased vibration couples with the liquid couplant 120 resulting in either or both a standing wave 132 of couplant to form generally above the defect 116 and/or couplant to be ejected or atomized 136 from the test specimen 108.

The cooling effect of the agitated couplant and/or of the atomized couplant 136 as it evaporates produces cold signatures which can be detected by the infrared camera. For example, ejected couplant 136 cools by evaporation and thus appears cold relative to the surface portion 124 in the infrared images acquired by the infrared camera 112.

Analyzing the infrared images for cold signatures can be performed manually by an inspector, automatically by a processor, a combination thereof, etc. Infrared images can also be analyzed to detect mode patterns of excitation in addition to detecting cold signatures.

In the illustrated embodiment, the system 100 includes a display screen 140 on which can be displayed infrared images, preferably in real-time, acquired by the camera 112. This, in turn, allows reliability to be increased because an inspector can analyze the real-time infrared images to locate and size defects.

In some embodiments, infrared contrast can be increased thus making the atomized couplant easier to identify by acquiring an infrared image of the liquid couplant before excitation and then subtracting therefrom infrared images of the excited liquid couplant acquired during the excitation.

In this exemplary manner, the system 100 is capable of detecting defects in the test specimen 108 without requiring heating of the test specimen 108 by the excitation source 104. Further, the thermal characteristics of the test specimen 108 do not generally affect the infrared aspect of the system 100 because infrared radiation does not readily transmit through water, among other liquid couplants which can be used in the system 100.

FIG. 3 illustrates another exemplary system 200 embodying at least one aspect of the invention. As shown in FIG. 3, the system 200 includes an excitation source 204 for exciting the test specimen 208. Preferably, the excitation source 204 is a source of ultrasonic energy, such as an ultrasonic welder or horn. Alternatively, other excitation sources can also be employed such as mechanical shakers and acoustic horns.

The system 200 can include a video camera 212 for visually detecting vibration effects, such as standing waves 232 and "geysers" 236 of couplant 220. In at least some embodiments, the vibration effects are readily detectable by the unassisted human eye 212' in which case the vibration effects can be visually detected by either or both the video camera 212 and/or an inspector visually observing the excited liquid couplant 220.

In other embodiments, the system does not include any video camera or other visual detection device for detecting the vibration effects. In such embodiments, the vibration effects (e.g., standing waves, "geysers") are detected by an inspector visually observing the excited liquid couplant.

Alternatively, a wide range of other devices and techniques can be used for detecting the defect signatures or vibration effects of the liquid couplant in response to the excitation including high speed photography, videography for motion analysis, specialized lenses, high speed analysis lighting, video imaging technologies, and specialized techniques such as Schlieren, streak, and pulsed laser illumination.

The system 200 also includes the liquid couplant 220 which is applied to the test specimen 208. In an exemplary embodiment, the liquid couplant 220 is water. In alternative embodiments, however, a wide range of other liquid couplants, preferably liquids non-reactive and non-contaminating to the test specimen, can be used including oils, glycerins, high purity alcohols, non-contaminating liquid chemicals, etc.

In operation, the system 200 can be used as follows to detect defects in the test specimen 208. A liquid detection medium 220 is applied to at least a first surface portion 224 of the test specimen 208. In an exemplary embodiment, the liquid couplant 220 is water misted onto the part surface 224.

The test specimen 208 is excited with the excitation source 204. In the illustrated embodiment, the test specimen 208 is acoustically excited with a preferably high energy ultrasonic source in contact with the test specimen 208. The source 204 preferably applies ultrasonic energy 228 to the test specimen 208 which propagates through the test specimen 208. The propagating energy 228 causes preferential, large amplitude vibrations generally above a defect 216 in the test specimen 208. The increased vibration couples with the liquid couplant 220 resulting in either or both a standing wave 232 of couplant to form generally above the defect 216 and/or couplant to be ejected or atomized 236 from the test specimen 208.

The camera 212 acquires images, preferably real-time images, of the liquid couplant 220. The images are analyzed for standing waves 232 of couplant and/or couplant ejected 236 from the test specimen 208. The images acquired by the camera 212 can be analyzed manually by an inspector, automatically by a processor, a combination thereof, etc.

In the illustrated embodiment, the system 200 includes a display screen 240 on which can be displayed images, preferably in real-time, acquired by the camera 212. This, in turn, allows reliability to be increased because an inspector can analyze the real-time images to locate and size defects.

Further, a real-time examination of the complete test specimen 208 can be performed by indexing the exciter 204 and camera 212 over the test specimen 208.

Additionally, or alternatively, the vibration effects in at least some embodiments are readily detectable by the unassisted human eye 212'. In which case, the inspector can perform a real-time examination by watching for the particular vibration effects indicative of the existence of defects in the test specimen 208.

Accordingly, various embodiments of the invention detect defects by analyzing the vibration effects on the liquid couplant without relying on heat generation by vibration. Because the excitation source does not need to dwell on the part surface to generate heat in the part, a test specimen can be inspected with shorter excitation times and shorter pulse durations. This, in turn, reduces the likelihood that the test specimen will be accidentally damaged from prolonged use of the excitation source.

Various embodiments can be used to examine thermally conductive materials with high diffusivity and/or shiny surfaces having low emissivity because the liquid couplant can provide a high emissivity coating to the shiny surface.

Various embodiments enable wide area defect detection that allows relatively large areas to be inspected in an efficient and timely manner.

The invention is applicable to a wide range of material types and structures including metals, composites, substrates, plastics, multilayer coatings, wood laminates, painted substrates, etc. Accordingly, the specific references to test specimen herein should not be construed as limiting the scope of the present invention to only one specific form/type of test specimen.

The invention is also applicable to a wide range of industries and industrial applications including aerospace, space, automotive, etc. Accordingly, the specific references to aircraft should not be construed as limiting the scope of the present invention to any specific industry or industrial application.

While various preferred embodiments have been described, those skilled in the art will recognize modifications or variations which might be made without departing from the inventive concept. The examples illustrate the invention and are not intended to limit it. Therefore, the description and claims should be interpreted liberally with only such limitation as is necessary in view of the pertinent prior art.

What is claimed is:

1. A method for detecting defects in a test specimen, the method comprising:
    applying a liquid detection medium to the test specimen;
    exciting the test specimen to cause the liquid detection medium to produce a defect signature for a defect in the test specimen; and
    monitoring the liquid detection medium for defect signatures produced by the liquid detection medium, said monitoring including monitoring the liquid detection medium to detect a temperature differential indicative of a defect in the test specimen,
    wherein:
    the defect signature comprises a cold signature; and
    the monitoring comprises thermally monitoring the liquid detection medium to detect cold signatures.

2. The method of claim 1, wherein the excitation of the test specimen causes liquid detection medium to be ejected from the test specimen at about the defect, the ejected liquid detection medium cooling by evaporation and producing the cold signature.

3. The method of claim 1, wherein the thermally monitoring comprises acquiring infrared images of the liquid detection medium.

4. The method of claim 3, wherein the acquiring comprises:
    acquiring an infrared image of the liquid detection medium before excitation;
    acquiring one or more infrared images of the liquid detection medium during excitation; and
    subtracting from the infrared image acquired before excitation the one or more infrared images acquired during excitation.

5. The method of claim 1, wherein the defect signature further comprises a vibrational mode pattern.

6. The method of claim 5, wherein the vibrational mode pattern comprises a standing wave of liquid detection medium on the test specimen generally above the defect.

7. The method of claim 5, wherein the vibrational mode pattern comprises an ejection of liquid detection medium from the test specimen at about the defect.

8. The method of claim 7, wherein the monitoring comprises visually monitoring the liquid detection medium to detect the ejection of liquid detection medium from the test specimen.

9. The method of claim 8, wherein the visually monitoring comprises acquiring real-time images of the liquid detection medium.

10. The method of claim 9, further comprising displaying the real-time images to an inspector.

11. The method of claim 1, wherein the applying comprises misting water on the test specimen.

12. The method of claim 1, wherein the exciting comprises ultrasonically exciting the test specimen.

13. The method of claim 1, wherein the test specimen comprises a composite structure.

14. The method of claim 1, wherein the liquid detection medium includes insoluble particles which form a visible pattern on the test specimen at about a defect after the excitation.

15. A method of detecting defects in a test specimen without having to rely on heating of the test specimen, the method comprising:
    applying a liquid couplant to at least a first surface portion of the test specimen;
    acoustically exciting the test specimen; and
    monitoring the liquid couplant for vibration effects which indicate defects in the test specimen, the vibration effects including an ejection of liquid couplant from the first surface portion, wherein the monitoring comprises thermally monitoring the liquid couplant for a cold signature.

16. The method of claim 15, wherein the excitation of the test specimen causes liquid couplant to be ejected from the first surface portion at about a defect, the ejected liquid couplant cooling by evaporation and producing the cold signature.

17. The method of claim 15, wherein the thermally monitoring comprises acquiring infrared images of the liquid couplant.

18. The method of claim 15, wherein the monitoring comprises visually monitoring the liquid couplant to detect the vibration effects.

19. The method of claim 18, wherein the visually monitoring comprises acquiring real-time images of the liquid couplant.

20. The method of claim 19, further comprising displaying the real-time images to an inspector.

21. The method of claim 15, wherein the applying comprises misting water on the first surface portion.

22. The method of claim 15, wherein the acoustically exciting comprises ultrasonically exciting the test specimen.

23. A method of detecting defects in a test specimen, the method comprising:
- applying a liquid couplant to at least a first surface portion of the test specimen;
- acoustically exciting the test specimen to cause an ejection of liquid from the first surface portion at about a defect in the test specimen, the ejected liquid cooling by evaporation and producing a cold signature for said defect; and
- thermally monitoring the liquid couplant to detect cold signatures produced by the liquid couplant.

24. The method of claim 23, wherein the thermally monitoring comprising acquiring and analyzing infrared images of the liquid couplant.

25. The method of claim 23, wherein the thermally monitoring comprises acquiring real-time infrared images of the liquid couplant and displaying the real-time infrared images to an inspector.

26. The method of claim 25, wherein the acquiring comprises:
- acquiring an infrared image of the liquid couplant before excitation;
- acquiring one or more infrared images of the liquid couplant during excitation; and
- subtracting from the infrared image acquired before excitation the one or more infrared images acquired during excitation.

27. A system for detecting defects in a test specimen without having to rely on heating of the test specimen, the system comprising:
- a liquid couplant on the test specimen;
- an exciter coupled to the test specimen to excite the test specimen to cause the liquid couplant to produce a defect signature for a defect in the test specimen; and
- a device to detect defect signatures produced by the liquid couplant in response to the excitation including at least one of an ejection of liquid couplant from the test specimen and a temperature differential indicative of a defect in the test specimen, the device comprising a camera for acquiring images of the defect signatures, wherein the camera comprises an infrared camera for acquiring infrared images of cold signatures produced by the liquid couplant in response to the acoustic excitation.

28. The system of claim 27, further comprising a display device for displaying the images to an inspector.

29. The system of claim 27, wherein the exciter comprises an ultrasonic welder.

* * * * *